United States Patent
Stohrer et al.

(10) Patent No.: US 7,173,149 B2
(45) Date of Patent: Feb. 6, 2007

(54) PROCESS FOR PREPARING ALKYNECARBOXYLIC ACIDS BY OXIDATION OF ALKYNE ALCOHOLS

(75) Inventors: Jürgen Stohrer, Pullach (DE); Elke Fritz-Langhals, Ottobrunn (DE); Christian Brüninghaus, Unterhaching (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 43 days.

(21) Appl. No.: 10/667,810

(22) Filed: Sep. 22, 2003

(65) Prior Publication Data

US 2004/0059154 A1  Mar. 25, 2004

(30) Foreign Application Priority Data

Sep. 25, 2002  (DE) ................. 102 44 633

(51) Int. Cl.
*C07C 51/16*  (2006.01)
(52) U.S. Cl. ............... 562/416; 562/405; 562/407; 562/510; 562/523; 562/538; 562/540; 562/598; 560/128; 560/203; 560/205; 560/208
(58) Field of Classification Search ............... 546/240; 560/128, 203, 205, 208; 562/405, 407, 416, 562/510, 523, 538, 540, 598
See application file for complete search history.

(56) References Cited

U.S. PATENT DOCUMENTS

| 6,127,573 | A | * | 10/2000 | Li et al. ............... 562/419 |
| 6,498,269 | B1 | * | 12/2002 | Merbouh et al. ........... 562/515 |
| 6,750,371 | B2 | * | 6/2004 | Fritz-Langhals et al. .... 568/471 |
| 2004/0063932 | A1 | * | 4/2004 | Zedda et al. ............... 540/472 |

FOREIGN PATENT DOCUMENTS

| EP | 1103537 | 5/2001 |
| EP | 1336599 | 8/2003 |
| WO | 99/52849 | 10/1999 |

OTHER PUBLICATIONS

Azerbaev et al. "Synthesis and reactions of acetylenic . . . " CA 79:126292 (1973).*
RN 2564-83-2.*
de Nooy et al. "Selective oxidation ofprimafy alcohols . . . " CA 123:340678 (1995).*
Harbeson et al. "Stereospecific synghesis . . . " CA 122:133766 (1995).*
Brochette et al. "Sonocatalysis of the . . . " 132:152042 (2000).*
Thaburet et al. "TEMPO mediated oxidation . . . " CA 1334:281053 (2001).*
Ullmann's Encyclopedia, 6$^{th}$ Edition, 2001, Electronic Release, "Carboxylic Acids, Aliphatic 5.2".
Houben-Weyl, vol. V12a, 4$^{th}$ Edition, 1977 "Alkynes".
Wolf. Chem. Ber. 1954, 87, 668.
Kauten and Schäfer, Tetrahedron, 1982, 38, 3299.
Heilbron, Jones and Sondheimer, J. Chem. Soc. 1949, 606.
T.W. Abbott et al., Org. Synth. Coll. vol. II, 1943, 10.
A.E.J. de Nooy, A.C. Besemer and H.V. Bekkum, Synthesis 1996, 1153.
G. Grigoropoulou et al., Chem. Commun. 2001, 547-548.
P.L. Anelli, C. Biffi, F. Montanari and S. Quici, J. Org. Chem. 1987, 52, 2559.
P. L. Anelli, F. Montanari and S. Quici, Org. Synth., 1990, 69, 212.
M. Zhao et al., J. Org. Chem. 1999, 64, 2564.
Straus et al., Ber. Dtsch. Chem. Ges. 1930, 1868.
Cirriminna et al., Chem. Commun. 2000, 1441.
Bolm et al., Chem. Commun. 1999, 1795.
Bobbitt et al., Chem. Commun. 1996, 2745.
Miyazawa and Endo, J. Molec. Catal. 49, 1988, L31.
M. J. Verhoef et al., "Studies in Surface Science and Catalysis", vol. 125, p. 465H.
D. Brunel et al., Studies in Surface Science and Catalysis, vol. 125, p. 237H.
Miyazawa and Endo, J. Polymer Sci., Polym. Chem. Ed. 23, 1985, 1527 and 2487.
T. Osa, Chem. Lett. 1988, 1423.
Ullmann's Encyclopedia, 6$^{th}$ Edition, Electronic Release, Chlorine Oxides and Chlorine Oxygen Acids 2-.4.
Ullmann's Encyclopedia, 6$^{th}$ Edition, 2002, Electronic Release, Phase Transfer Catalysis.
Ullmann's Encyclopedia of Industrial Chemistry, vol. B4.

* cited by examiner

*Primary Examiner*—Celia Chang
(74) *Attorney, Agent, or Firm*—Collard & Roe, P.C.

(57) ABSTRACT

A process for preparing alkynecarboxylic acids includes the oxidation of an alkyne alcohol with a hypohalite in the presence of a nitroxyl compound at a pH of greater than 7 with continual addition of the alkyne alcohol and of the hypohalite to the reaction mixture.

18 Claims, No Drawings

PROCESS FOR PREPARING ALKYNECARBOXYLIC ACIDS BY OXIDATION OF ALKYNE ALCOHOLS

BACKGROUND OF THE INVENTION

1. Field of the Invention

The present invention relates to a process for oxidizing alkyne alcohols (alkynols) to alkynecarboxylic acids (alkynoic acids).

2. The Prior Art

Alkynoic acids are important synthetic building blocks. Of particular importance are propiolic acid and acetylenedicarboxylic acid which are used to build rings in cycloadditions, in particular Diels-Alder reactions and 1,3-dipolar cycloadditions, and in nucleophilic addition reactions (overview in Ullmann's Encyclopedia, 6th Edition, 2001 electronic release; "Carboxylic acids, aliphatic 5.2").

The oxidation of alkynols to alkynoic acids has been described in the prior art (overviews in Ullmann's Encyclopedia, 6th Edition, 2001 electronic release; "Carboxylic acids, aliphatic 5.2"; Houben-Weyl volume V/2a, 4th edition 1977, "Alkynes")

For example, propiolic acid is obtained by anodic oxidation of propargyl alcohol (Wolf, Chem. Ber. 1954, 87, 668). Acetylenedicarboxylic acid is likewise obtained by anodic oxidation of 2-butyne-1,4-diol. However, the electrochemical process has the disadvantage of the use of lead dioxide anodes which leads to the contamination of the electrolytes with lead ions and can generally only be used in production at high capital cost. In addition, the decarboxylation of the product proceeding as a side reaction leads to technically undesired formation of large amounts of $CO_2$ and acetylene which have to be disposed of. Also, the yields in the case of propiolic acid are relatively low (less than 50%).

The analogous anodic oxidation on nickel oxide anodes (Kaulen and Schäfer, Tetrahedron 1982, 38, 3299) requires low current densities and very large electrode surface areas, which leads to a further increase in the capital costs. In addition, the activated nickel surface is passivated during the electrolysis and frequently has to be regenerated which leads to an increase in the process costs.

Propiolic acid can also be obtained by oxidation of propargyl alcohol with Cr(VI) oxide in sulfuric acid. Good yields can be achieved, but large amounts of toxic and environmentally hazardous heavy metal salts have to be disposed of. The analogous reaction of 2-butyne-1,4-diol leads to only a 23% yield of acetylenedicarboxylic acid (Heilbron, Jones and Sondheimer, J. Chem. Soc. 1949, 606).

A known nonoxidative preparation process of propiolic acid and acetylenedicarboxylic acid is the reaction of metal acetylides with $CO_2$. However, this requires the use of expensive metal bases and, owing to the use of acetylene, is technically not without risk. The yields of this process in the case of propiolic acid are likewise only 50%.

In a further process for preparing acetylenedicarboxylic acid, fumaric acid is initially converted with bromine to meso-dibromosuccinic acid, which is then isolated and dehalogenated in a further stage. This two-stage process is time-consuming and laborious (T. W. Abbott et al., Org. Synth. Coll. Vol. II, 1943, 10).

The prior art discloses general oxidation processes of alcohols to carboxylic acids with the aid of nitroxyl compounds as catalysts, in particular with the aid of nitroxyls such as TEMPO (2,2,6,6-tetramethylpiperidine 1-oxyl) and its derivatives (overview in A. E. J. de Nooy, A. C. Besemer and H. V. Bekkum, Synthesis 1996, 1153).

TEMPO-catalyzed oxidations of alcohols to carboxylic acids are carried out in biphasic systems, for example methylene chloride/water and also in the presence of phase transfer catalysts (G. Grigoropoulou et al., Chem. Commun. 2001, 547–548, P. L. Anelli, C. Biffi, F. Montanari and S. Quici, J. Org. Chem. 1987, 52, 2559). The stoichiometric oxidant used is predominantly bleaching liquor (hypochlorite solution).

In the customary performance of these syntheses in biphasic systems, the oxidant dissolved in the aqueous phase, which is adjusted to a pH range of 8.5–9, is added in a batch process to an initially charged organic phase which comprises the alcohol to be oxidized, the phase transfer catalyst and the nitroxyl compound.

The prior art discloses that such oxidation processes using bleaching liquor and nitroxyl compounds are generally to be considered as unsuitable for the oxidation of unsaturated alcohols (on this subject, compare in particular P. L. Anelli, C. Biffi, F. Montanari and S. Quici, J. Org. Chem. 1987, 52, 2559; P. L. Anelli, F. Montanari and S. Quici, Org. Synth., 1990, 69, 212).

For instance, the reaction of an alkyne alcohol without terminal alkyne group (3-phenylpropynol) with bleaching liquor and TEMPO by the process disclosed in the prior art affords only unacceptable low yields of from 5 to a maximum of 20 mol % of the alkynoic acid (M. Zhao et al., J. Org. Chem. 1999, 64, 2564; WO 99/52849).

The oxidation of alkynols with terminal alkyne group with bleaching liquor and TEMPO at pH>7 has hitherto not been described.

A possible cause is the sensitivity disclosed by the literature of terminal alkyne groups toward bleaching liquor. The CH groups of terminal alkynes are easily converted, for example, to chloroalkynes by bleaching liquor, which are particularly labile in alkaline media and tend to decompose (Straus et al., Ber. Dtsch. Chem. Ges. 1930, 1868). This is especially true in the case of alkaline reaction conditions, since the acidic terminal acetylene unit is particularly readily halogenated. The resulting 3-halopropiolates are additionally compounds which decompose easily and have a tendency toward explosion.

SUMMARY OF THE INVENTION

It is therefore an object of the present invention to provide a process for preparing alkynoic acids by the oxidation of alkyne alcohols which avoids the disadvantages known from the prior art.

Surprisingly, it has now been found that the disadvantages of the processes disclosed by the prior art can be avoided by not initially charging all of the alkyne alcohol to be oxidized in the presence of nitroxyl compounds at pH>7, as in the processes disclosed by the prior art, but rather by adding it like the oxidant to the reaction mixture continually.

The invention therefore provides a process for preparing alkynecarboxylic acids, characterized by the oxidation of an alkyne alcohol with a hypohalite in the presence of a nitroxyl compound at a pH of >7, with continual addition of the alkyne alcohol and of the hypohalite to the reaction mixture.

The continual addition of the alkyne alcohol and of the hypohalite to the reaction mixture in accordance with the process according to the invention may be continuous or discontinuous.

In the case of continuous addition, a greater or lesser amount, depending on various reaction parameters to be monitored, of alkyne alcohol and hypohalite is metered in constantly.

In the case of discontinuous addition, alkyne alcohol and hypohalite, depending on various reaction parameters to be monitored, are metered in intermittently.

The continual addition of the alkyne alcohol and of the hypohalite to the reaction mixture, both in the case of the continuous and the discontinuous method, may be parallel or alternating.

In the case of alternating addition, alkyne alcohol and hypohalite are not metered in simultaneously and/or are not metered in in the same molar amounts within a time interval.

In the case of parallel addition, alkyne alcohol and hypohalites are always metered in simultaneously (parallel addition).

The reaction parameters to be monitored in the case of the continual addition of the alkyne alcohol and of the hypohalites to the reaction mixture relate in particular to the pH of the reaction mixture and also to its temperature.

In a particularly preferred embodiment of the invention, alkyne alcohol and hypohalite are added continually and in parallel.

In a preferred embodiment of the process according to the invention, an initial charge can be used which may comprise water, one or more inert organic solvents, acids, bases or buffer mixtures, portions or the entire amounts of the nitroxyl compounds and phase transfer catalysts used, and also portions of the alkyne alcohol used or portions of the oxidant used.

The conversion is then effected by further continual addition of the alkyne alcohol and of the hypohalite to the initial charge.

The use of an initial charge is recommended in particular for the beginning of a continuous reaction.

It has also been found that, surprisingly, alkyne alcohols can also be oxidized to alkynecarboxylic acids without the use of phase transfer catalysts.

Surprisingly, the oxidation is possible even in an aqueous monophasic system.

It has also been found that, surprisingly, alkyne alcohols having terminal alkyne groups can also be oxidized in excellent yields at pH>7 by the process according to the invention.

In general, the alkyne alcohols (alkynols) to be oxidized are compounds which contain at least one monovalent group of the formula —$CH_2$—OH and at least one divalent group of the formula —C≡C—.

The alkyne alcohols to be oxidized are preferably linear or branched primary alcohols having 3–30 carbon atoms, cyclic alcohols having 8–30 carbon atoms or alcohols which are substituted by an aromatic radical and have 6–30 carbon atoms, each of which contains a group of the formula —C≡C—, where one hydrogen or more than one hydrogen may be independently replaced by F, Cl, Br, I, $NO_2$, ONO, CN, NC or SCN, or where one $CH_2$ group or more than one $CH_2$ group may be independently replaced by O, NH, C=O, $CO_2$, S, S=O, $SO_2$, P=O or $PO_2$, or one CH group or more than one CH group may be independently replaced by N, B or P, or quaternary carbon atoms may be replaced by Si, Sn or Pb.

Particular preference is given to the alkyne alcohols $R^1$—C≡C—$CH_2$OH, $R^1$—C≡C—$CH_2$—$CH_2$OH, or $R^1$C≡C—$CH_2$—$CH_2$—$CH_2$OH, $R^1$—O—$CR^2R^3$—C≡C—$CH_2$OH, $R^1$—O—$CR^2R^3$—C≡C—$CH_2$—$CH_2$OH or $R^1$—O—$CR^2R^3$—C≡C—$CH_2$—$CH_2$—$CH_2$OH where $R^1$ is H, methyl, ethyl or a linear or branched $C_3$–$C_{12}$ radical, in particular an n-propyl, isopropyl, 1- or 2-n-butyl, 2-methylpropyl, 1-, 2- or 3-n-pentyl, 2- or 3-methyl-1-butyl, 1,2-dimethylpropyl, tert-butyl, neopentyl or tert-pentyl radical, or a saturated or unsaturated cyclic $C_3$–$C_{12}$ radical, in particular a cyclopropyl, cyclobutyl, cyclopentyl, cyclopentenyl, methylcyclopentyl, methylcyclopentenyl, cyclohexyl, cyclohexenyl, methylcyclohexyl, methylcyclohexenyl, cycloheptyl, cyclooctyl, cyclododecyl or decalinyl radical, or a $C_6$–$C_{12}$-aryl or aralkyl radical, in particular a phenyl, benzyl, phenethyl, naphthyl, biphenylyl, anthryl, phenanthryl, azulenyl, anthraquinonyl, 2-, 3- or 4-methylphenyl, 2,3-, 2,4- or 2,5-dimethylphenyl or mesitylyl radical, or a $C_6$–$C_{12}$-heteroaryl or heteroaralkyl radical, in particular a furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl or phenoxazinyl radical, or is $R^4R^5R^6$Si where $R^4$, $R^5$ and $R^6$ are each independently $C_1$–$C_{12}$-alkyl, in particular methyl, ethyl, n-propyl, isopropyl or n-butyl, or $C_1$–$C_{12}$-oxyalkyl, in particular methoxy, ethoxy, n-propoxy, isopropoxy or butoxy, $C_6$–$C_{12}$-aryl or $C_7$–$C_{12}$-aralkyl, in particular phenyl or benzyl, and $R^2$ and $R^3$ are each independently H, $C_1$–$C_{12}$-alkyl, in particular methyl, ethyl, n-propyl or n-butyl, $C_6$–$C_{12}$-aryl or $C_7$–$C_{12}$-aralkyl, in particular phenyl, 2-, 3- or 4-methylphenyl or benzyl, and to alkynols $R^7$—CO—C≡C—$CH_2$OH, $R^7$—CO—C≡C—$CH_2$—$CH_2$OH or $R^7$—CO—C≡C—$CH_2$—$CH_2$—$CH_2$OH where $R^7$ is methyl, ethyl or a linear or branched $C_3$–$C_{12}$ radical, in particular an n-propyl, isopropyl, 1- or 2-n-butyl, 2-methylpropyl, 1-, 2- or 3-n-pentyl, 2- or 3-methyl-1-butyl, 1,2-dimethylpropyl, tert-butyl, neopentyl or tert-pentyl radical, or a saturated or unsaturated cyclic $C_3$–$C_{12}$ radical, in particular a cyclopropyl, cyclobutyl, cyclopentyl, cyclopentenyl, methylcyclopentyl, methylcyclopentenyl, cyclohexyl, cyclohexenyl, methylcyclohexyl, methylcyclohexenyl, cycloheptyl, cyclooctyl, cyclododecyl or decalinyl radical or a $C_6$–$C_{12}$-aryl or aralkyl radical, in particular a phenyl, benzyl, phenethyl, naphthyl, biphenylyl, anthryl, phenanthryl, azulenyl, anthraquinonyl, 2-, 3- or 4-methylphenyl, 2,3-, 2,4- or 2,5-dimethylphenyl or mesitylyl radical, or a $C_6$–$C_{12}$-heteroaryl or heteroaralkyl radical, in particular a furyl, pyrrolyl, thienyl, benzofuranyl, isobenzofuranyl, benzothiyl, isobenzothienyl, indolyl, isoindolyl, indolizinyl, pyrazolyl, imidazolyl, oxazolyl, thiazolyl, isoxazolyl, isothiazolyl, indazolyl, carbazolyl, benzotriazolyl, purinyl, pyridyl, pyridazinyl, pyrimidyl, pyrazinyl, quinolinyl, isoquinolinyl, quinoxalinyl, quinazolinyl, cinnolinyl, phenanthridinyl, acridinyl, 1,10-phenanthrolinyl, phenazinyl, phenothiazinyl or phenoxazinyl radical, and also to Cl—$CH_2$—C≡C—$CH_2$OH and HO—$CH_2$—C≡C—$CH_2$OH.

Very particular preference is given to 2-propyn-1-ol, but-3-yn-1-ol, but-2-yn-1-ol, pent-4-yn-1,2-diol, 2-butyn-1, 4-diol, 4-chloro-2-butyn-1-ol, 4-acetoxy-2-butyn-1-ol, 4-t-butyldimethylsiloxy-2-butyn-1-ol, 3-phenyl-2-propyn-1-ol, 3-trimethylsilyl-2-propyn-1-ol, 3-t-butyldimethylsilyl-2-propyn-1-ol.

In particular, 2-propyn-1-ol, 4-chloro-2-butyn-1-ol or 2-butyn-1,4-diol are suitable, most preferably 2-propyn-1-ol or 2-butyn-1,4-diol.

The nitroxyl compound used as an oxidation catalyst is generally a di-tert-alkylnitroxyl compound.

It is preferably a nitroxyl compound of the general formula I

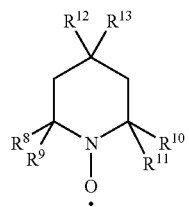

I where the radicals $R^8$, $R^9$, $R^{10}$ and $R^{11}$ are each independently $C_1$–$C_{12}$-alkyl or $C_2$–$C_{12}$-alkenyl or $C_6$–$C_{12}$-aryl or aralkyl, and the radicals $R^{12}$ and $R^{13}$ are each independently hydrogen, OH, CN, halogen, linear or branched, saturated or unsaturated $C_1$–$C_{20}$-alkyl, $C_6$–$C_{20}$-aryl, $C_6$–$C_{20}$-hetaryl or $C_6$–$C_{20}$-aralkyl, $OR^{14}$, O—$COR^{14}$, O—$COOR^{14}$, $OCONHR^{14}$, COOH, $COR^{14}$, $COOR^{14}$, $CONHR^{14}$ where $R^{14}$ is a linear or branched, saturated or unsaturated $C_1$–$C_{20}$-alkyl radical, or a $C_6$–$C_{20}$-aryl, $C_3$–$C_{20}$-hetaryl or $C_6$–$C_{20}$-aralkyl radical, —(O—$CH_2$—$CH_2$)$_n$—$OR^{15}$, —(O—$C_3H_6$)$_n$—$OR^{15}$, —(O—($CH_2$)$_4$)$_n$—$OR^{15}$, —O—$CH_2$—CHOH—$CH_2$—(O—$CH_2$—$CH_2$—)$_n$—$OR^{15}$ where $R^{15}$ is hydrogen, $C_1$–$C_{20}$-alkyl, $C_6$–$C_{20}$-aralkyl, where n=1 to 100, or $CH_2$—CHOH—$CH_3$ or $CH_2$—CHOH—$CH_2$—$CH_3$, $NR^{16}R^{17}$, $NHCOR^{16}$, $NHCOOR^{16}$, $NHCONHR^{16}$, where $R^{16}$ and $R^{17}$ are each independently a linear or branched, saturated or unsaturated $C_1$–$C_{20}$-alkyl radical, a $C_6$–$C_{12}$-cycloalkyl radical, or a $C_6$–$C_{20}$-aryl, $C_3$–$C_{20}$-hetaryl or $C_6$–$C_{20}$-aralkyl radical, where the radicals $R^{12}$ and $R^{13}$ may also be linked to a ring, and where the radicals $R^{12}$ and $R^{13}$ in turn may also be substituted by COOH, OH, $SO_3H$, CN, halogen, primary, secondary or tertiary amino or quaternary ammonium, or the radicals $R^{12}$ and $R^{13}$ together may also be =O, =$NR^{18}$, =N—$OR^{18}$, =N—N=$CR^{18}R^{19}$ where $R^{18}$ and $R^{19}$ are each independently hydrogen, $C_1$–$C_{20}$-alkyl or $C_6$–$C_{20}$-aralkyl.

Preference is further given to the nitroxyl compound being two molecules of the formula I which are linked via a bridge =N—N= in the 4-position.

Preference is further given to the nitroxyl compound being two or more molecules of the formula I which are bonded to each other via one of the two radicals $R^{12}$ and $R^{13}$. The linking radical is particularly preferably O-alkyl-O, O—$CH_2$-aryl-$CH_2$—O, or a bridge of the general formula (O—($CH_2$)$_n$—O)$_m$ where n=2 to 4 and m=2 to 50, in particular m=2 to 20.

In a further embodiment, the nitroxyl compound is a polymeric structure comprising compounds of the formula I which are linked via the radicals $R^{11}$ or $R^{12}$ or $R^{11}$ and $R^{12}$.

Those skilled in the art are familiar with a variety of such compounds from the prior art (EP 1103537, Cirriminna et al., *Chem. Commun.* 2000, 1441; Bolm et al., *Chem. Commun.* 1999, 1795; Bobbitt et al., *Chem. Commun.* 1996, 2745, Miyazawa and Endo, *J. Molec. Catal.* 49, 1988, L31; M. J. Verhoef et al. in "Studies in Surface Science and Catalysis", Vol. 125, p. 465 ff; D. Brunel et al. in "Studies in Surface Science and Catalysis", Vol. 125, p. 237 ff; Miyazawa and Endo, *J. Polymer Sci., Polym. Chem. Ed.* 23, 1985, 1527 and 2487; T. Osa, *Chem. Lett.* 1988, 1423).

In particular, PIPO (polyamine-immobilized piperidinyl oxyl), $SiO_2$-supported TEMPO, polystyrene- and polyacrylic acid-supported TEMPO are particularly suitable.

Particularly preferred nitroxyl compounds are compounds of the general formula I, where $R^8$, $R^9$, $R^{10}$ and $R^{11}$ are each $CH_3$ and $R^{12}$ and $R^{13}$ are each independently hydrogen, OH, $OR^{14}$, O—$COR^{14}$, O—$COOR^{14}$, $OCONHR^{14}$, where $R^{14}$ is a linear or branched, saturated or unsaturated $C_1$–$C_{20}$-alkyl radical, or a $C_6$–$C_{20}$-aryl or $C_6$–$C_{20}$-aralkyl radical, —(O—$CH_2$—$CH_2$)$_n$—$OR^{15}$, —(O—$C_3H_6$)$_n$—$OR^{15}$, —(O—($CH_2$)$_4$)$_n$—$OR^{15}$, —O—$CH_2$—CHOH—$CH_2$—(O—$CH_2$—$CH_2$—)$_n$—$OR^{15}$ where $R^{15}$ is hydrogen, $C_1$–$C_{10}$-alkyl or $C_6$–$C_{10}$-aralkyl, where n=1 to 100, or $CH_2$—CHOH—$CH_3$ or $CH_2$—CHOH—$CH_2$—$CH_3$, $NR^{16}R^{17}$, $NHCOR^{17}$, $NHCOOR^{17}$, $NHCONHR^{17}$, where $R^{16}$ and $R^{17}$ are each independently hydrogen, a linear or branched, saturated or unsaturated $C_1$–$C_{20}$-alkyl radical, a $C_6$–$C_{12}$-cycloalkyl radical or a $C_6$–$C_{20}$-aryl or $C_6$–$C_{20}$-aralkyl radical.

Further particularly preferred nitroxyl compounds are compounds of the general formula I where $R^8$, $R^9$, $R^{10}$ and $R^{11}$ are each $CH_3$, where $R^{12}$ and $R^{13}$ together form ketal groups of the formulae O—$CHR^{20}CHR^{21}$—O or O—$CH_2CR^{22}R^{23}$—$CH_2$—C where $R^{20}$, $R^{21}$, $R^{22}$ and $R^{23}$ are each independently hydrogen or $C_1$–$C_3$-alkyl, or where the radicals $R^{12}$ and $R^{13}$ together are =O.

A preferred nitroxyl compound is in particular a compound of the general formula I where $R^8$, $R^9$, $R^{10}$ and $R^{11}$ are each $CH_3$ where $R^{12}$ is hydrogen and $R^{13}$ is hydrogen, OH, $OR^{14}$, O—$COR^{14}$, where $R^{14}$ is a linear or branched saturated $C_1$–$C_{12}$-alkyl radical, or is an aryl or benzyl radical, —(O—$CH_2$—$CH_2$)$_n$—$OR^{15}$, —(O—$C_3H_6$)$_n$—$OR^{15}$, —(O—($CH_2$)$_4$)$_n$—$OR^{15}$, —O—$CH_2$—CHOH—$CH_2$—(O—$CH_2$—$CH_2$—)$_n$, —$OR^{15}$ where n=1 to 50 and $R^{15}$ is hydrogen or $CH_2$—CHOH—$CH_3$ or $CH_2$—CHOH—$CH_2$—$CH_3$ $NR^{16}R^{17}$, $NHCOR^{17}$ where $R^{16}$ and $R^{17}$ are each independently a linear or branched, saturated $C_1$–$C_{12}$-alkyl radical or an aryl or benzyl radical.

Examples of nitroxyl compounds which can be used with particular preference are TEMPO, 4-hydroxy-TEMPO, 4-oxo-TEMPO, 4-amino-TEMPO, 4-acetamido-TEMPO, 4-benzoyloxy-TEMPO, 4-acetoxy-TEMPO and PIPO.

4-Hydroxy-TEMPO is most preferred.

The nitroxyl compound is generally used in amounts of from 0.01 to 50 mol %, preferably in amounts of from 0.1 to 20 mol %, more preferably in amounts of from 1 to 10 mol %, based on the amount of alkyne alcohol to be oxidized.

The nitroxyl compound may be dissolved in the reaction component comprising the alkyne alcohol or in the aqueous phase or used in supported form as an independent phase. The nitroxyl compound can be initially charged in its entirety or be added continuously to the reaction mixture, optionally also in the form of an additional liquid feed.

The oxidant used is preferably a compound selected from the group of the hypohalites, in particular hypochlorite, hypobromite and hypoiodite or their mixtures. A particularly preferred oxidant is hypochlorite. Preferred counterions are hydrogen, sodium, potassium, calcium or tetraalkylammonium and particular preference is given to sodium and calcium.

Those skilled in the art are familiar with suitable hypohalites and hypohalite preparations from the prior art (*Ullmann Encyclopedia, 6th Edition*, 2002 electronic release; "Chlorine oxides and Chlorine oxygen acids 2.–4.").

In a particularly preferred embodiment, technical hypohalite solutions and suspensions, in particular technical hypochlorite solutions, are used.

The oxidant used may also be generated in situ, in particular electrochemically, by hydrolysis, in particular by hydrolysis of N-chlorine compounds, or by redox reactions such as, in the case of hypochlorite or hypobromite solutions, by the disproportionation of chlorine or bromine in aqueous alkaline solution, or by the redox reaction between hypochlorite and bromide which leads to the formation of hypobromite.

The oxidants used, in particular hypochlorite and hypobromite are preferably used as aqueous solutions in concentrations of from 0.1 M up to their respective saturation concentration.

The pH of aqueous solutions or suspensions of the oxidant is generally from 7 to 14. However, it is not necessary to adjust the pH of the oxidant to a particular value, so that adjustment of the pH of the oxidant beforehand can advantageously be dispensed with.

The pH of the aqueous phase of the reaction mixture in the process according to the invention is thus a pH of greater than 7, preferably between pH 7 and 14, more preferably between pH 7 and 11, in particular between pH 8 and 10.

Preference is given to using from 2 to 5 mol equivalents of the hypohalite based on the number of functional groups to be oxidized, in particular from 2 to 3 mol equivalents of the hypohalite based on the number of functional groups to be oxidized.

The desired pH of the reaction mixture is generally attained by adding a base, preferably sodium hydroxide, potassium hydroxide, calcium hydroxide, calcium carbonate, sodium carbonate, more preferably sodium hydroxide and calcium carbonate.

The desired pH of the reaction mixture can also be attained by adding a buffer, preferably by adding a carbonate or phosphate buffer. From the group of the carbonate buffers, particularly suitable are sodium carbonate/sodium hydrogencarbonate or calcium carbonate/calcium hydrogencarbonate, in particular calcium carbonate/calcium hydrogencarbonate. From the group of the phosphate buffers, particularly suitable are sodium salts or potassium salts of phosphoric acid.

Further possible additives are salts, for examle alkali metal, alkaline earth metal or ammonium halides, carbonates or sulfates.

The reaction temperature is generally from −10 to +80° C., preferably from −5 to +40° C., more preferably from −5 to +20° C.

The process according to the invention is preferably carried out at atmospheric pressure.

Generally, the components involved in the reaction in the process according to the invention can be reacted in one phase or divided between a plurality of phases.

In one possible embodiment, the process according to the invention is carried out in a liquid phase which comprises water and one or more water-miscible solvents (cosolvents).

In one embodiment of the monophasic reaction, the alkyne alcohol to be oxidized is added in pure form or eluted with water or with one or more inert, water-miscible solvents, as reaction component 1, and the oxidant as reaction component 2.

The inert, water-miscible solvents are preferably selected from the group of the ethers, in particular THF and 1,4-dioxane, the nitrites, in particular acetonitrile or alcohols, for example tert-butanol, isopropanol or DMF, DMSO.

The alkyne alcohol to be oxidized can be used in concentrations of between 0.1 and 100% by weight, preferably between 20 and 100% by weight, based on reaction component 1.

In a further possible embodiment of the process according to the invention, the reactions are carried out in multiphasic systems.

In this case, preference is given to using at least one aqueous phase and one organic phase.

In a particularly preferred embodiment, the alkyne alcohol is used as reaction component 1, optionally in pure form or dissolved in one or more solvents. Preference is given to using water-immiscible organic solvents. The resulting phase separation may be caused by a water-immiscible alkyne alcohol as a reactant.

The aqueous phase as reaction component 2 comprises the oxidant.

Preferred organic solvents for carrying out the process according to the invention in a multiphasic system are one or more solvents selected from the group of ethers, in particular THF, methyl t-butyl ether, dimethoxymethane and diethyl ether, chlorohydrocarbons, e.g. methylene chloride, esters, e.g. ethyl acetate, alcohols, e.g. tert-butanol, hydrocarbons, e.g. toluene, cyclohexane, heptane, and also dimethyl sulfoxide (DMSO), acetonitrile.

The alcohol to be oxidized can be used in concentrations of between 0.1 to 100% by weight, based on reaction component 1, preferably between 20 to 100% by weight.

In a further preferred embodiment of the reaction in multiphasic systems, the process according to the invention is carried out in the presence of one or more phase transfer catalysts. Suitable phase transfer catalysts are known to those skilled in the art (see, for example, "Phase transfer catalysis", *ULLMANN'S ENCYCLOPEDIA OF INDUSTRIAL CHEMISTRY*, 6th Edition electronic release, 2002). Preferred phase transfer catalysts are quaternary ammonium salts, for example tetrabutylammonium chloride, tetrabutylammonium bromide, tetrabutylammonium sulfate, methyltrioctylammonium chloride, methyltributylammonium chloride, benzyltrimethylammonium chloride, triethylbenzylammonium chloride, and crown ethers, e.g. 18-crown-6.

The phase transfer catalyst can be used in amounts of between 0.1 to 10 mol %, based on the alkyne alcohol to be oxidized, when the process according to the invention is carried out in the presence of an aqueous and also of at least one organic phase. The phase transfer catalyst may be disposed in the initial charge, but can also be added to the reaction component 1 or 2.

The process according to the invention can be carried out in batch mode or in the form of a continuous reaction.

In a preferred embodiment of the process according to the invention, the phases involved in the reaction are added continuously.

In this case, alkyne alcohol and hypohalite are added in the form of a continual addition in accordance with the invention and the resulting reaction solution is simultaneously removed continuously from the reactor.

The nitroxyl compound is likewise added continuously or used in the form of a steady-state phase. The favorable pH range for the reaction can be maintained by continuous metered addition by which bases or acids are added to the reaction mixture in such a way that there is a constant pH of >7 in the reaction mixture.

The continuous reactors which are suitable for continuous reaction are known to those skilled in the art. An overview of the most important embodiments can be found, for example, in "*Ullmann's Encyclopedia of Industrial Chemistry*", Vol. B4.

Preferred embodiments of a process carried out continuously are continuous stirred reactors, continuous loop reactors, continuous stirred tanks or stirred tank batteries or a process carried out with the aid of centrifugal pumps.

When the process according to the invention is carried out continuously, the residence time set is between 0.1 sec and 10 h, preferably between 1 sec and 1 h, more preferably between 1 sec and 20 min.

When the process described is performed as a continuous process, this allows the additional advantages of efficient heat dissipation from the strong exothermic reaction process.

The relative ratio of the volume streams of the two reaction components can be kept constant, but can also be changed depending on the contents which are established in the reaction mixture of yet to be converted alkyne alcohol, alkynoic acid and oxidant.

The metering rate of the two reaction components is preferably such that the reaction mixture remains within the preferred temperature range, taking into account the available cooling performance.

The advantages of the process according to the invention are the provision of a process for oxidizing alkyne alcohols which is simple to carry out from a technical point of view and uses the inexpensive oxidant hypohalite, and solves the problems known from the pior art.

In particular, the combination of measures of controlling the pH of the aqueous phase of the reaction mixture and of continually adding the two reactants hypohalite and alkyne alcohol to the reaction mixture allow high yields of alkynecarboxylic acids to be achieved.

By the process according to the invention, using inexpensive bleaching liquor (e.g. sodium hypochlorite) which is easy to use from a technical point of view, it is possible to oxidize even readily water-soluble alkynols and alkynols having terminal alkyne groups in a technically simple manner and outstanding yield to the corresponding alkynecarboxylic acids.

Especially substrates having terminal alkyne groups were hitherto not obtainable by the reactions which could be realized on the industrial scale and were economically viable in oxidative processes known from the prior art.

In addition, the process according to the invention is applicable to a wide range of substrates having terminal and nonterminal alkyne groups.

For example, propiolic acid can be obtained by the process according to the invention from propargyl alcohol in a 75–90% yield, and acetylenedicarboxylic acid from butynediol in a 50–70% yield.

The wastewater resulting from the reaction contains only salts such as NaCl which are easily disposed of and can therefore be disposed of without any problem. The process according to the invention also avoids the safety risk of large initial charges of alkynols which, in the event of metering errors of the oxidant, may lead to uncontrolled reactions (for example to the formation of chloroalkyne compounds).

The oxidative processes known from the prior art were only possible in batch mode and therefore of little interest with regard to industrial scale realizability and economic viability.

All of the above-mentioned symbols of the above-mentioned formulae are each defined independently of one another.

The examples which follow serve to further illustrate the invention, without being a limitation thereof.

DETAILED DESCRIPTION OF THE PREFERRED EMBODIMENTS

COMPARATIVE EXAMPLE 1

Oxidation of 2-propyn-1-ol to Propiolic Acid with the Initial Charging of All of the Alkyne Alcohol 19.6 g (350 mmol) of 2-propyn-1-ol are dissolved together with 3.0 g (17.4 mmol) of 4-hydroxy-TEMPO and 5.9 g (17.5 mmol) of tetrabutylammonium hydrogensulfate in 132 ml of water and 132 ml of $CH_2Cl_2$ and cooled to 5° C. (reaction component 1).

14.0 g (350 mmol) of NaOH are dissolved in 427 g of 2.4 M (approx. 350 ml, 840 mmol) of sodium hypochlorite solution (technical bleaching liquor; pH 14) and cooled to 5° C. (reaction component 2).

All of reaction component 1 is initially charged in a flask with mechanical stirrer and jacket cooling.

Reaction component 2 is added in such a way that the internal temperature does not rise above 10° C. During this time, the pH of the reaction mixture is maintained between pH 8 and pH 10 by adding 20% sulfuric acid.

On completion of addition, stirring is continued at 10° C. for a further 10 min. An analysis of the two phases shows that approximately 91% of the alcohol used has been converted. The organic phase contains 1.3 mol % of propargyl propiolate. The aqueous phase contains 46 mol % of propiolic acid.

EXAMPLE 1

Oxidation of 2-propyn-1-ol to Propiolic Acid in a Biphasic System and in the Presence of Phase Transfer Catalyst 19.6 g (350 mmol) of 2-propyn-1-ol are dissolved together with 3.0 g (17.4 mmol) of 4-hydroxy-TEMPO in 20 g of $CH_2Cl_2$ (reaction component 1).

14.0 g (350 mmol) of NaOH are dissolved in 436 g of 2.4 M (approx. 357 ml, 857 mmol) of sodium hypochlorite solution (technical bleaching liquor; pH 14) and cooled to 5° C. (reaction component 2).

In a flask equipped with mechanical stirrer, 5.9 g (17.4 mmol) of tetrabutylammonium hydrogensulfate are initially charged in 132 ml of water and 132 ml of $CH_2Cl_2$, and cooled to 5° C. Reaction component 1 and 2 are added in parallel with good stirring and cooling in such a way that the internal temperature does not rise above 10° C. During this time, the pH of the reaction mixture is kept between pH 8 and pH 10 by adding 20% by weight sulfuric acid.

On completion of addition, stirring is continued at 10° C. for a further 10 min.

After removing the organic phase (contains the phase transfer catalyst), the aqueous phase is adjusted to pH 0 using hydrochloric acid (20% by weight) and extracted three times using 100 ml of ethyl acetate each time. The aqueous phase is discarded.

The ethyl acetate phases are combined and, after partial distillative removal of the ethyl acetate, provide an approx. 50% solution of propiolic acid in ethyl acetate which contains 19.5 g (278 mmol) of propiolic acid (yield 79 mol %).

EXAMPLE 2

Oxidation of 2-propyn-1-ol to Propiolic Acid in a Biphasic System without Phase Transfer Catalyst 19.6 g (350 mmol) of 2-propyn-1-ol are dissolved together with 3.0 g (17.4 mmol) of 4-hydroxy-TEMPO in 20 g of $CH_2Cl_2$ and cooled to 5° C. (reaction component 1).

14.0 g (350 mmol) of NaOH are dissolved in 440 g of 2.3 M (approx. 360 ml, 828 mmol) of sodium hypochlorite solution (technical bleaching liquor; pH 14) and cooled to 5° C. (reaction component 2).

A glass flask equipped with mechanical stirrer is initially charged with 132 ml of water and 132 ml of $CH_2Cl_2$, and cooled to 5° C. Reaction component 1 and reaction component 2 are added in parallel with intensive stirring and cooling in such a way that the internal temperature does not rise above 10° C. In parallel, continual addition of 20% by weight sulfuric acid keeps the pH of the reaction mixture between 8 and 10.

On completion of addition, stirring is continued for another 10 min.

After removal of the organic phase (contains 4 mol % of propargyl propiolate), the aqueous phase is adjusted to pH 0 using hydrochloric acid (20% by weight) and extracted three times with 100 ml of ethyl acetate each time. The aqueous phase is discarded.

The ethyl acetate phases are combined and, after partial distillative removal of the ethyl acetate, provide an approx. 50% solution of propiolic acid in ethyl acetate which contains 18.3 g (261 mmol) of propiolic acid (yield 75 mol %).

EXAMPLE 3

Oxidation of 2-propyn-1-ol to Propiolic Acid in an Aqueous Monophasic System 19.6 g (350 mmol) of 2-propyn-1-ol are dissolved together with 3.0 g (17.4 mmol) of 4-hydroxy-TEMPO in 20 ml of water (reaction component 1).

14.0 g (350 mmol) of NaOH are dissolved in 440 g of 2.4 M (approx. 360 ml, 864 mmol) of sodium hypochlorite solution (technical bleaching liquor; pH 14) and cooled to 5° C. (reaction component 2).

A glass flask equipped with mechanical stirrer is initially charged with 132 ml of water and cooled to 5° C. Reaction component 1 and reaction component 2 are added in parallel with intensive cooling and stirring in such a way that the internal temperature does not rise above 10° C. In parallel, continual addition of 20% by weight sulfuric acid keeps the pH of the reaction mixture between 8 and 10.

On completion of the addition of the reaction components, stirring is continued for a further 10 min and any hypochlorite still present is destroyed using the sodium hydrogensulfite solution.

The reaction mixture is extracted using 150 ml $CH_2Cl_2$. After removing the organic phase (contains 0.9 mol % of propargyl propiolate), the aqueous phase is adjusted to pH 0 using hydrochloric acid (20% by weight) and extracted three times using 100 ml of ethyl acetate each time. The aqueous phase is discarded.

The ethyl acetate phases are combined and, after partial distillative removal of the ethyl acetate, provide an approx. 50% solution of propiolic acid in ethyl acetate which contains 20.3 g (290 mmol) of propiolic acid (yield 83 mol %). This solution can be used directly for the preparation of ethyl propiolate.

To obtain pure propiolic acid, this solution is admixed with 100 ml of toluene and then ethyl acetate is distilled off. The propiolic acid is then isolated from the remaining solution by distillation.

EXAMPLE 4

Continuous Oxidation of 2-propyn-1-ol to Propiolic Acid 408 g (7 278 mmol) of 2-propyn-1-ol are mixed with 37.6 g (218 mmol) of 4-hydroxy-TEMPO and diluted with 408 g of ethyl acetate (reaction component 1).

10.9 kg of 2.04 M (approx. 8 900 ml, 18.2 mol) of sodium hypochlorite solution (technical bleaching liquor; pH 14) cooled to 5° C. are prepared (reaction component 2).

The reaction apparatus consists of a 500 ml reaction vessel which is equipped with bottom outlet, jacket cooling and mechanical stirrer and, to improve the cooling performance, is connected to an external cooler, through which the reaction mixture is pumped continually and recycled into the reaction vessel.

The apparatus is initially charged with 900 ml of 0.1 M phosphate buffer (pH 7) and cooled to 5° C.

With vigorous stirring, reaction component 1 at 7.2 g/min (corresponding to 61 mmol of 2-propyn-1-ol/min) and reaction component 2 at 91 g/min (corresponding to 152 mmol hypochlorite/min) are pumped into the reaction vessel, from which corresponding portions of the reaction mixture are continuously removed.

The temperature is kept between 15 and 20° C. by cooling. The pH of the reaction mixture is kept at 8.5 with the aid of a titrator which supplies 25% by weight sodium hydroxide solution.

An analysis of the collected product solution shows that a total of 469 g (6 696 mmol) of propiolic acid have been formed (yield 92 mol %).

EXAMPLE 5

Oxidation of 2-butyn-1-ol to 3-methylpropiolic Acid in a Biphasic System and in the Presence of Phase Transfer Catalysts 12.3 g (175 mmol) of 2-butyn-1-ol are dissolved together with 1.5 g (8.7 mmol) of 4-hydroxy-TEMPO in 13 g of $CH_2Cl_2$ (reaction component 1).

7.0 g (175 mmol) of NaOH are dissolved in 220 g of 2.4 M (approx. 180 ml, 432 mmol) of sodium hypochlorite solution (technical bleaching liquor; pH 14) and cooled to 5° C. (reaction component 2).

In a flask equipped with mechanical stirrer, 3.5 g (8.7 mmol) of Aliquot 336 are initially charged in 66 ml of water and 66 ml of $CH_2Cl_2$, and cooled to 5° C. Reaction components 1 and 2 are added in parallel with good stirring and cooling in such a way that the internal temperature does not rise above 10° C. During this time, the pH of the reaction mixture is kept between pH 8 and pH 10 by adding 20% by weight sulfuric acid.

On completion of addition, stirring is continued at 10° C. for a further 10 min.

After removal of the organic phase (contains 9 mol % of 3-methylpropanal), the aqueous phase is adjusted to pH 0 using hydrochloric acid (20% by weight) and extracted three times using 50 ml of ethyl acetate each time. The aqueous phase is discarded.

The ethyl acetate phases are combined and, after partial distillative removal of the ethyl acetate, provide an approx. 50% solution of 3-methylpropiolic acid in ethyl acetate which contains 12.1 g (144 mmol) of 3-methylpropiolic acid (yield 82 mol %).

EXAMPLE 6

Oxidation of 2-butyn-1-ol to 3-methylpropiolic Acid in a Biphasic System 12.3 g (175 mmol) of 2-butyn-1-ol are dissolved together with 1.5 g (8.7 mmol) of 4-hydroxy-TEMPO in 13 g of $CH_2Cl_2$ (reaction component 1).

7.0 g (175 mmol) of NaOH are dissolved in 220 g of 2.4 M (approx. 180 ml, 432 mmol) of sodium hypochlorite solution (technical bleaching liquor; pH 14) and cooled to 5° C. (reaction component 2).

A flask equipped with mechanical stirrer is initially charged with 66 ml of water and 66 ml of $CH_2Cl_2$, and cooled to 5° C. Reaction components 1 and 2 are added in parallel with good stirring and cooling in such a way that the internal temperature does not rise above 10° C. During this time, the pH of the reaction mixture is kept between pH 8 and pH 10 by adding 20% by weight sulfuric acid.

On completion of addition, stirring is continued at 10° C. for another 10 min.

After removal of the organic phase (contains 35 mol % of 3-methylpropanal), the aqueous phase is adjusted to pH 0 using hydrochloric acid (20% by weight) and extracted three times with 50 ml of ethyl acetate each time. The aqueous phase is discarded.

The ethyl acetate phases are combined and, after partial distillative removal of the ethyl acetate, provide an approx. 50% solution of 3-methylpropiolic acid in ethyl acetate which contains 5.8 g (69 mmol) of 3-methylpropiolic acid (yield 39 mol %).

EXAMPLE 7

Oxidation of 2-propyn-1-ol to Propiolic Acid in an Aqueous Monophasic System using an Aqueous Initial Charge and Batchwise Addition of the Reactants 30 g (535 mmol) of 2-propyn-1-ol are dissolved together with 4.6 g (26.7 mmol) of 4-hydroxy-TEMPO in 30 g of water (reaction component 1).

625 g of 2.4 M (approx. 500 ml, 1 200 mmol) of sodium hypochlorite solution (technical bleaching liquor; pH 14) cooled to 5° C. are prepared (reaction component 2).

In a 2 l glass flask equipped with mechanical stirrer, 17.8 g (100 mmol) of $Na_2HPO_4.2H_2O$ are dissolved in 800 ml of water, adjusted to pH 7 using phosphoric acid and cooled to 5° C. With intensive cooling and stirring, in each case approx. 45 ml of reaction component 2 and approx. 6 ml of reaction component 1 are added dropwise in alternation in such a way that the internal temperature does not rise above 10° C. In parallel, the continual addition of 20% by weight sodium hydroxide solution keeps the pH of the reaction mixture between 7 and 10.

On completion of addition of the reaction components, stirring is continued for a further 10 min. Evaluation of the propiolic acid content of the aqueous phase by means of HPLC gives a crude yield of 90 mol % of propiolic acid.

The reaction mixture is extracted using 300 ml $CH_2Cl_2$. After removing the organic phase, the aqueous phase is adjusted to pH 0 using hydrochloric acid (20% by weight) and extracted three times with 300 ml of ethyl acetate each time. The aqueous phase is discarded.

The ethyl acetate phases are combined and, after partial distillative removal of the ethyl acetate, provide an approx. 50% solution of propiolic acid in ethyl acetate which contains 31.2 g (446 mmol) of propiolic acid (yield 83 mol %).

EXAMPLE 8

Oxidation of 2-butyne-1,4-diol to acetylene-dicarboxylic Acid in an Aqueous Monophasic System Using Acetamido-TEMPO 14.4 g (167 mmol) of 2-butyn-1,4-diol are dissolved together with 2.14 g (10.0 mmol) of 4-acetamido-TEMPO in 94 ml of water (reaction component 1).

6.68 g (167 mmol) of NaOH are dissolved in 337 ml (0.741 mol) of sodium hypochlorite solution (approx. 2.2 M technical bleaching liquor; pH 14) and cooled to 5° C. (reaction component 2).

A flask equipped with mechanical stirrer is initially charged with 50 ml of water and cooled to 3° C. Reaction components 1 and 2 are added in parallel with good stirring and cooling in such a way that the internal temperature does not rise above 10° C. During this time, the pH of the reaction mixture is kept in the range from 8.5 to 10 by adding 20% sodium hydroxide solution. A total of approx. 15 ml of sodium hydroxide solution are consumed.

On completion of addition, stirring is continued for another 20 min.

The reaction mixture contains 11.4 g of acetylene-dicarboxylic acid in solution and 2.1 g of acetylene-dicarboxylic acid in the precipitate formed (overall yield 13.5 g, 71%). Extraction is effected using 300 ml of MTBE, then the pH of the aqueous reaction mixture is adjusted to pH 0 with stirring in an ice bath using conc. sulfuric acid, and extraction is effected by shaking 3 times using 100 ml of MTBE each time. The MTBE extracts of the acidic reaction mixture are concentrated by evaporation. 11.1 g of acetylenedicarboxylic acid are obtained in the form of a colorless solid.

Accordingly, while a few embodiments of the present invention have been shown and described, it is to be understood that many changes and modifications may be made thereunto without departing from the spirit and scope of the invention as defined in the appended claims.

What is claimed is:

1. A process for preparing alkynecarboxylic acids, comprising oxidizing an alkyne alcohol with a hypohalite in the presence of a nitroxyl compound at a pH of greater than 7 within a reaction mixture; and using from 2 to 5 mol equivalents of the hypohalite bsed on the number of functional groups to be oxidized, and continuously adding the alkyne alcohol and the hypohalite to the reaction mixture, wherein said nitroxyl compound is selected from the group consisting of (2,2,6,6-tetramethylpiperidine-1-oxyl also known as TEMPO, 4-hydroxy-TEMPO, 4-oxo-TEMPO, 4-amino-TEMPO, 4-acetamido-TEMPO, 4-benzyloxy-TEMPO, and 4-acetoxy-TEMPO, and wherein the reaction mixture is in two phases.

2. The process as claimed in claim 1, wherein at least one phase transfer catalyst is used.

3. The process as claimed in claim 1, comprising removing the reaction mixture continuously.

4. The process as claimed in claim 1, wherein the pH of aqueous phase of the reaction mixture is between 7 and 11.

5. The process as claimed in claim 1, wherein the nitroxyl compound used is 4-hydroxy-TEMPO.

6. The process as claimed in claim 1, wherein reaction temperature is between −5° C. and 20° C.

7. The process as claimed in claim 1, wherein from 2 to 3 mol equivalents of the hypohalite are used based on the number of functional groups to be oxidized.

8. The process as claimed in claim 1, wherein the alkyne alcohol used is selected from the group consisting of 2-propyn-1-ol and 2-butyne-1,4-diol.

9. The process as claimed in claim 1, wherein the reaction is carried out in the presence of a substance selected from the group consisting of phosphate buffer and calcium carbonate.

10. A process for preparing alkynecarboxylic acids, comprising initially charging less than all of an alkyne alcohol to be oxidized in a reaction mixture;

oxidizing the alkyne alcohol with a hypohalite in the presence of a nitroxyl compound at a pH of greater than 7 within the reaction mixture;

using from 2 to 5 mol equivalents of the hypohalite based on the number of functional groups to be oxidized, and continuously adding remainder of the alkyne alcohol and the hypohalite to the reaction mixture, wherein said nitroxyl compound is selected from the group consisting of (2,2,6,6-tetrametylpiperidine-1-oxyl) also known as TEMPO, 4-hydroxy-TEMPO, 4-oxo-TEMPO, 4-amino-TEMPO, 4-acetamido-TEMPO, 4-benzyloxy-TEMPO, and 4-acetoxy-TEMPO, and wherein the reaction mixture is in two phases.

11. The process as claimed in claim 10, wherein at least one phase transfer catalyst is used.

12. The process as claimed in claim 10, comprising removing the reaction mixture continuously.

13. The process as claimed in claim 10, wherein the pH of aqueous phase of the reaction mixture is between 7 and 11.

14. The process as claimed in claim 10, wherein the nitroxyl compound used is 4-hydroxy-TEMPO.

15. The process as claimed in claim 10, wherein reaction temperature is between −5° C. and 20° C.

16. The process as claimed in claim 10, wherein from 2 to 3 mol equivalents of the hypohalite are used based on the number of functional groups to be oxidized.

17. The process as claimed in claim 10, wherein the alkyne alcohol used is selected from the group consisting of 2-propyn-1-ol and 2-butyne-1,4-diol.

18. The process as claimed in claim 10, wherein the reaction is carried out in the presence of a substance selected from the group consisting of phosphate buffer and calcium carbonate.

* * * * *